United States Patent
Drott et al.

(10) Patent No.: US 10,143,697 B2
(45) Date of Patent: Dec. 4, 2018

(54) PHARMACEUTIC COMPOSITION COMPRISING OF HDAC INHIBITOR AND A STEROID AND THE USE THEREOF

(71) Applicant: VALCURIA AB, Lund (SE)

(72) Inventors: Kristina Drott, Lund (SE); Thomas Relander, Lund (SE)

(73) Assignee: VALCURIA AB, Lund (SE)

( * ) Notice: Subject to any disclaimer, the term of this patent is extended or adjusted under 35 U.S.C. 154(b) by 0 days.

(21) Appl. No.: 15/074,768

(22) Filed: Mar. 18, 2016

(65) Prior Publication Data
US 2016/0271146 A1    Sep. 22, 2016

Related U.S. Application Data

(62) Division of application No. 14/005,933, filed as application No. PCT/SE2012/050306 on Mar. 20, 2012, now abandoned.

(60) Provisional application No. 61/454,751, filed on Mar. 21, 2011.

(30) Foreign Application Priority Data

Dec. 15, 2011   (SE) ...................................... 1151196

(51) Int. Cl.
| | | |
|---|---|---|
| *A61K 31/573* | (2006.01) | |
| *A61K 31/167* | (2006.01) | |
| *A61K 31/165* | (2006.01) | |
| *A61K 45/06* | (2006.01) | |
| *A61K 38/07* | (2006.01) | |
| *A61K 38/12* | (2006.01) | |
| *A61K 31/18* | (2006.01) | |
| *A61K 31/19* | (2006.01) | |
| *A61K 31/404* | (2006.01) | |
| *A61K 31/437* | (2006.01) | |
| *A61K 31/4402* | (2006.01) | |
| *A61K 39/395* | (2006.01) | |
| *G01N 33/50* | (2006.01) | |

(52) U.S. Cl.
CPC .......... *A61K 31/573* (2013.01); *A61K 31/165* (2013.01); *A61K 31/167* (2013.01); *A61K 31/18* (2013.01); *A61K 31/19* (2013.01); *A61K 31/404* (2013.01); *A61K 31/437* (2013.01); *A61K 31/4402* (2013.01); *A61K 38/07* (2013.01); *A61K 38/12* (2013.01); *A61K 39/3955* (2013.01); *A61K 45/06* (2013.01); *G01N 33/5011* (2013.01)

(58) Field of Classification Search
CPC ................ A61K 31/573; A61K 31/167; A61K 31/4402; A61K 31/165; A61K 31/19; A61K 31/18; A61K 45/06
See application file for complete search history.

(56) References Cited

U.S. PATENT DOCUMENTS

| | | | |
|---|---|---|---|
| 8,828,392 B2 | 9/2014 | Lichenstein et al. | |
| 2005/0038113 A1* | 2/2005 | Groner | A61K 31/19 514/546 |
| 2008/0274120 A1* | 11/2008 | Lichenstein | A61K 31/10 424/145.1 |
| 2010/0093610 A1 | 4/2010 | Vrolijk et al. | |

FOREIGN PATENT DOCUMENTS

JP    2006-327980    12/2006

OTHER PUBLICATIONS

Vigushin et al Clinical Cancer Research 7; 971-976 (2001).*
Thurn et al. Future Oncol. (Feb. 2011):7(2):263-283 as pp. 1-34).*
Leukemia, 2010, vol. 24, No. 10, p. 1760-1768.
Munster, et al., "Clinical and Biological Effects of Valproic Acid as a Histone Deacetylase Inhibitor on Tumor and Surrogate Tissues: Phase I/II Trial of Valproic acid and Epirubicin/FEC", Apr. 1, 2009, pp. 2488-2496, vol. 15, No. 7, Clin Cancer Res.

* cited by examiner

*Primary Examiner* — Shirley V Gembeh
(74) *Attorney, Agent, or Firm* — Stephen J. Weyer, Esq.; Stites & Harbison, PLLC

(57) ABSTRACT

A pharmaceutical composition comprises a HDAC inhibitor, a pharmaceutically acceptable acid or a salt thereof or a mixture thereof and a steroid or a pharmaceutically acceptable salt thereof as well use of said pharmaceutical composition for the treatment of cancer as a pretreatment prior to other treatments. Said HDAC inhibitor or steroid may alternatively be administrated separately prior to additional treatments.

8 Claims, 1 Drawing Sheet

PHARMACEUTIC COMPOSITION COMPRISING OF HDAC INHIBITOR AND A STEROID AND THE USE THEREOF

CROSS REFERENCE TO RELATED APPLICATION

This is a divisional application of U.S. patent application Ser. No. 14/005,933 filed Sep. 18, 2013, a national stage of PCT/SE2012/050306, filed Mar. 20, 2012, which claims the benefit of Ser. No. 61/454,751, filed Mar. 21, 2011, all incorporated by reference.

FIELD OF INVENTION

The invention relates to a pharmaceutical composition comprising a HDAC inhibitor, a pharmaceutically acceptable acid or a salt thereof or a mixture thereof and a steroid or a pharmaceutically acceptable salt thereof as well use of said pharmaceutical composition for the treatment of cancer as a pretreatment prior to other treatments. Said HDAC inhibitor or steroid may alternatively be administered separately prior to additional treatments.

BACKGROUND OF INVENTION

Cancer can be defined as an abnormal growth of cells which exhibit signs of uncontrolled proliferation and disturbed programmed cell death. From a classical view, sequential genetic events lead to malignant transformation, resulting in a cell clone that does not respect the integrity of other cells and tissues, and may eventually metastasize. Cancer can involve any tissue of the body and have many different forms in each body area.

Malignant lymphoma can be defined as a malignant transformation of the lymphatic cells of the hematopoietic system. Lymphomas can be divided into aggressive lymphomas and indolent lymphomas. Aggressive lymphomas are characterized by a rapid growth pattern, and can have dramatic clinical features. However, aggressive lymphomas can reach a complete cure by treatment with chemotherapy, radiotherapy and monoclonal antibodies. In contrast, indolent lymphomas (e.g., follicular lymphomas) have a slow growth pattern, and usually a more modest clinical presentation. However, although indolent lymphomas cannot reach a complete cure by standard lymphoma treatment, they can sometimes be cured by allogeneic stem cell transplantation. The median survival time for follicular lymphomas is 8-10 years. Diffuse large B cell lymphoma and Hodgkin lymphoma belong to the group of aggressive lymphomas, while follicular lymphoma and chronic lymphocytic leukaemia are indolent lymphomas. Myelomas consist of malignantly transformed plasmacells. They are related to indolent lymphomas, but are usually considered an entity of their own. The prognosis is pessimistic, with a median survival time of 5-7 years.

Diffuse Large B-cell Lymphoma (DLBCL) is the most frequent subtype of malignant lymphoma, with an incidence of about 500 cases/year in Sweden. DLBCLs constitute 60-70% of the group of aggressive lymphomas. The median age at diagnosis is 70 years, and DLBCL is slightly more common in males than in females. Standard first line treatment of DLBCL is chemotherapy consisting of a combination of cyclophosphamide, doxorubicin, vincristine and prednisone (CHOP). During recent years addition of the CD20 antibody rituximab has become international clinical standard (R-CHOP), leading to improved progression-free, event-free, disease-free and overall survival (Morrison, *Expert Rev Anticancer Ther*, 2008; 8(10): pp. 1651-1658). Still, since as many as 45% of patients die from their disease, there is a pronounced clinical need to increase progression-free survival in DLBCL patients.

Regulation of DNA transcription is complex and the mechanisms involved are only partially known. Histone Deacetylases (HDACs) can regulate expression of tumour suppressor genes and activities of transcription factors involved in both cancer initiation and progression. HDACs act through alteration of either DNA or the structural components of chromatin by histone deacetylation, thus affecting the three dimensional conformation of DNA without changing or interrupting its sequence (epigenetic modifications). It has also been suggested that they may alter the sensitivity to DNA damaging chemotherapy through modulation of chromatin structure. Along these lines, several in vitro studies have suggested that HDAC inhibitors can synergize with chemotherapy.

During recent years numerous HDAC inhibitors have been developed. They can be divided into four classes; hydroxamic acids/carbamic acids, cyclic peptides, aliphatic acids and benzamides. For example, vorinostat and romidepsin are approved for the treatment of cutaneous T-cell lymphoma lymphoma by the FDA (Food and drug administration), and are currently evaluated in the treatment of other malignancies.

The clinically most well-known inhibitor is the anticonvulsant valproic acid, which has been utilized in the treatment of epilepsy since the 1970s. Valproic acid belongs to the aliphatic acid class of inhibitors.

EP1 427 403 discloses the use of valproic acid (VPA) and pharmaceutically acceptable salts thereof for the manufacture of a medicament for the treatment of human cancer in combination with irradiation treatment wherein the human cancer is selected from the group consisting of breast cancer, colon cancer, head and neck cancer, small cell lung carcinoma and cancer of blood cells. According to EP1602371, VPA could also be used in combinatorial therapy with one or several other anti-cancer treatments which target mechanisms strikingly different from each other such as chemotherapeutic and cytotoxic reagents, differentiation-inducing reagents (e.g. retinoic acid, vitamin D, cytokines), hormonal therapy, immunological approaches and, more recently, the development of anti-angiogenic approaches and gene therapy.

US2008/0194690 discloses the use of an HDAC inhibitor, i.e., certain carbamic acid compounds, such as belinostat (PXD101) in combination with cyclodextrin, arginine or meglumine for the treatment of a number of diseases, including cancer, wherein the solubility of the HDAC inhibitor is enhanced by the addition of one or more of cyclodextrin, arginine or meglumine.

SUMMARY OF THE INVENTION

The invention relates to the unique finding that a combination of a HDAC inhibitor together with a steroid will improve the survival of a patient suffering from cancer such as lymphoma. The compounds are pharmaceutically acceptable compounds and are to be administrated at least prior to further treatments as a pretreatment. The substances are administrated together or separately and administrated as pharmaceutically acceptable compounds.

It has been found that the steroid could be utilized to increase the response from the patient upon treatment with the HDAC inhibitor as well as reduce the side-effects such as somnolence.

In a first aspect, the invention relates to a pharmaceutical composition comprising a HDAC inhibitor, an acid or a salt thereof or a mixture thereof and a steroid or a salt thereof.

In a second aspect the invention relates to the use of the composition as defined above for the treatment of cancer.

Thus, by providing such a pharmaceutical composition or the use of such a composition the survival rate for a person suffering from cancer such as lymphoma is increased as well as it is for the first time possible to treat elder people, requiring a lower dose of chemotherapy, with maintained efficacy.

In a third aspect the invention relates to a kit, comprising at least one pharmaceutical composition comprising a HDAC inhibitor, an acid or a salt thereof or a mixture thereof and a steroid or a salt thereof.

In a fourth aspect the invention relates to a kit comprising at least one suitable container or suitable packaging comprising a HDAC inhibitor, an acid or a salt thereof or mixture thereof and at least one suitable container or suitable packaging comprising a steroid or a salt thereof.

By providing such a kit it will be easy for a human being suffering from cancer to perform the pretreatment prior to additional treatment at the hospital.

In a fifth aspect the invention relates to a method of evaluating a substance effect on the CHOP-sensitivity of cell lines, comprising the steps of
  a. Providing a cell line selected from the group consisting of WSU-NHL, Karpas-422, ULA, SU-DHL-5 and SU_DHL-8
  b. Adding a combination of cyclophosphamide, doxorubicin, vincristin and prednisolone
  c. Adding a substance to be evaluated to each cell line
  d. And evaluating the viability of the cells.

In a final aspect a method of treating a human being suffering from cancer by administrating a pharmaceutical compositing comprising a HDAC inhibitor, an acid or a salt thereof or a mixture thereof and a steroid or a salt thereof. The pharmaceutical composition may be used in combination with one or more other treatments including chemotherapy, immunotherapy. The chemotherapy may be for example CHOP (cyclophosphamide, doxorubicin, vincristine and prednisone) and the immunotherapy may be a CD20antibody.

BRIEF DESCRIPTION OF THE DRAWINGS

The application will be described with reference to the following drawings as follows.

DETAILED DESCRIPTION OF THE INVENTION

HDAC and Steroid

Figure 1:
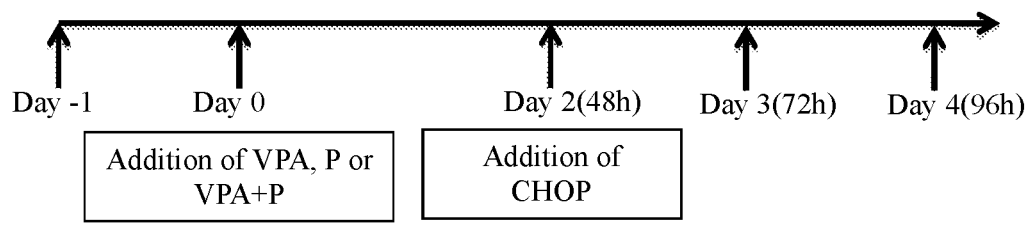
FIG. 1 shows different combinations of Valproic acid (VPA), prednisolone and CHOP applied to WSU-NHL cells in accordance with the present invention.

In a first aspect the invention relates to a pharmaceutical composition comprising a HDAC inhibitor, acid or a salt thereof or a mixture thereof and a steroid or a salt thereof. The HDAC inhibitor may be hydroxamic acid/carbamic acid, cyclic peptide, aliphatic acid or benzamide compound, such as vorinostat, romidepsin, valproic acid, aspanobinostat, belinostat, entinostat and resminostat, wherein some of them are used trademarks. Further the HDAC inhibitor may be valproic acid, such as sodium valproate or magnesium valproate or mixtures thereof. Examples includes vorinostat (marketed under the trade mark Zolinza® in the US), romidepsin (marketed under the trade mark Istodax® in the US), panobinostat. One form of valproic acid is when it is mixed with sodium valproate, i.e., a mixture of the acid and salt (valproate semisodium) and marketed under the various brand names Depakote, Depakote ER, Depakene, Depacon, Depakine, Valparin, Stavzor and Ergenyl. Sodium Valproate is marketed in Sweden as Absenor, Depakine, Orfiril. Valproic acid is marketed in Sweden as Ergenyl and Depakine.

The steroid to be used in the invention may be selected among the glucocorticoids and includes prednisone, prednisolone, dexamethasone and betamethasone. In one example the HDAC inhibitor is valproic acid and the steroid is prednisone.

Additional Ingredients

The pharmaceutical composition defined above may further comprise one or more other pharmaceutical acceptable pharmaceutical ingredients, such as a pharmaceutically acceptable diluent, carrier, excipient and buffer. "Pharmaceutically acceptable" means a non-toxic compound that does not decrease the effectiveness of the biological activity of the active ingredients. Such pharmaceutically acceptable additives, diluents buffers, carriers or excipients are well-known in the art (see Remington's Pharmaceutical Sciences, 18th edition, A.R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffering agents are magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "diluent" is intended to mean an aqueous or non-aqueous solution with the purpose of diluting the compounds in the pharmaceutical preparation. The diluent may be one or more of saline, water, polyethylene glycol, propylene glycol or ethanol.

The excipient may be one or more of carbohydrates, surfactants, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Administration Form

The pharmaceutical formulations according to the invention may be administered locally or systemically. Routes of administration include topical, ocular, nasal, pulmonar, buccal, parenteral (intravenous, subcutaneous, and intramuscular), oral, vaginal and rectal. Most commonly used being oral administration.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the manner of administration, the nature and severity of the disorder. Depending on the general health, sex, age and body weight of the patient different doses may be needed. The administration of the dose can be carried out both by single administration in the form of an individual dose unit or else several smaller dose units and also by multiple administration of subdivided doses at specific intervals. The active compounds or substances may also be administrated together or separately depending on the administration form.

Suitable preparation forms are, for example granules, powders, tablets, coated tablets, (micro) capsules, microgranulates effervescent powders or granules, suppositories, injectable solution in ampule form and also preparations with protracted release of active compounds, in whose preparation excipients, diluents or carriers are customarily used as described above. Other preparations may be those which give rise to different release profiles of the active ingredients which are well-known for a person skilled in the art examples includes sustained-release, sustained-action, extended-release, time-release or timed-release, controlled-release, modified release, or continuous-release. The advantages of sustained-release tablets or capsules are that they can often be taken less frequently than immediate-release formulations of the same drug, and that they keep steadier levels of the drug in the bloodstream. Today, most time-release drugs are formulated so that the active ingredient is embedded in a matrix of insoluble substance(s) (various: some acrylics, even chitin; these substances are often patented) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation is also regarded as a more complete technology to produce complex dissolution profiles. Through coating an active pharmaceutical ingredient around an inert core, and layering it with insoluble substances to form a microsphere it is possible to obtain more consistent and replicable dissolution rates. All of those being well-known for a person skilled in the art.

One Example of a Preparation Form is an Effervescent Product.

Effervescence is the reaction (in water) of acids and bases producing carbon dioxide. Examples of acids used in this reaction are citric acid, tartaric acid, malic acid, fumaric acid, adipic acid, acid citrates, succinic acid and mixtures thereof. Citric acid is the most commonly used, and it imparts a citrus-like taste to the product. Examples of bases used in the effervescent reaction are sodium carbonate, potassium carbonate, sodium bicarbonate, potassium bicarbonate, calcium bicarbonate, magnesium carbonate, sodium glycocarbonate, carboxylysine and mixtures thereof. Sodium bicarbonate is very common in effervescent formulas.

The compounds may be mixed together in the effervescent product or alternatively separated from each other. One example being when the two active substances are encapsulated separately from each other and the resulting effervescent product gives rise to different release profiles of the two active substances/ingredients.

The Effervescent Product may be in the Form of a Powder or as a Tablet.

If the product is a tablet it may comprise at least one additive selected from the group comprising binders, lubricants, emulsifiers fillers, surfactants (e.g., polysorbate 80 and sodium lauryl sulfate), flavours, aromas (examples of ingredients giving taste) (such as orange, lemon, bergamon, grapefruit, banana, apricot and strawberry) and colours, including natural or synthetic ones, vitamins, sweeteners (examples of ingredients giving taste) (acesulfame potassium, sodium saccharin, aspartame, stevia and surcalose), nutritional additives (e.g antioxidants, peptides), and mixtures thereof.

Substances giving taste, colour or antioxidative properties to the effervescent composition can be plant polyphenols coming from natural sources such as blueberries, cranberries, grapes and tea leaves.

Additionally the tablet may contain various lubricants suitable for use in the composition including water dispersible, water soluble, water insoluble lubricants and combinations thereof. Examples of useful water soluble lubricants include sodium benzoate, polyethylene glycol, L-leucine, adipic acid, and combinations thereof.

The tablet may also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. The effervescent agent may also comprise vitamins, and minerals.

The manufacturing process for the production of effervescent products involves some critical steps that need to be addressed carefully during formulation and manufacturing which is well known for a person skilled in the art. Production of effervescent products must occur in very low humidity areas. The best way to produce an effervescent product is in an environment where humidity is under strict control.

The process of producing tablets, known as "tableting" or "compressing" requires addition of pharmaceutical excipients well known to a person skilled in the art of powders like mixing, granulation and tableting. It is common practice in tablet production to add a lubricant after granulation; the most commonly used substance is magnesium stearate. During effervescent production, substances such as magnesium stearate can generate a problem since they are insoluble in water and, consequently, a film will form on top of the water after the tablet has dissolved. Strategies to overcome this problem are the use of other lubricants that are soluble in water; for example, a mixture of spray dried L-leucine and polyethylene glycol. Alternatively, not using any lubricant has the advantage of avoiding the blending step, but the disadvantage of special requirements for the production.

Amounts and Doses

The HDAC inhibitor will be administrated in different amounts depending on which HDAC inhibitor will be used. This is well known for a person skilled in the art. The same applies for the steroid. The active ingredients could be administrated together or separately. However, below follows a number of examples of amounts that could be utilized.

Examples of administration include administration of prednisone or prednisolone in an amount of 20 to 200 mg per day, such as 50-200, 100-150, 30, 40, 50, 60, 70, 80, 90, 100, 110, 120, 130, 140, 150, 160, 170, 180, 190 or 200 mg Betamethason may be administered in an amount of 4 to 32 mg per day, such as 10-25, 10-20, 5, 6, 7, 8, 9, 10, 11, 12, 13, 14, 15, 16, 17, 18, 19, 20, 21, 22, 23, 24, 25, 26, 27, 28, 29, 30, 31 Or 32 mg. Dexamethasone may be administered in an amount of 10 to 80 mg per day, such as 20-70, 10, 20, 30, 40, 50, 60, 70 or 80 mg. Prednisone may be administrated as a single dose or if needed multiple doses.

The HDAC inhibitor such as Valproic acid may be administrated orally or intravenously in ranges from about 500 mg to about 15000 mg per day, such as from about 4000 mg to about 15000 mg per day, such as from about 400 mg to about 3000 mg per day. For example, oral dosages can be about 800, about 1600, about 2400, about 3000, about 6000, about 9000, about 15000 mg per day. It is understood that the total amount per day can be administered in a single dose or can be administered in multiple dosing such as twice, three, four or five times per day.

The HDAC inhibitor such as Belinostat may be administrated orally in ranges from about 6 mg to about 3000 mg per day, such as from about 40 mg to about 3000 mg per day, such as from about 400 mg to about 3000 mg per day. For example, oral dosages can be about 4, about 40, about 400, about 800, about 1600, about 2400, about 2800 or about 3000 mg per day. It is understood that the total amount per day can be administered in a single dose or can be administered in multiple dosing such as twice, three, or four times per day.

One example of the administration of HDAC inhibitors or pharmaceutically acceptable salts thereof, steroids or pharmaceutically acceptable salts thereof may be that they are administrated alone or in combination at least once daily, such as during morning time, about 5 to 8 in the morning. However, the administration of any of the substances may occur 1, 2, 3, 4 or even up to 5 times daily. Examples of administration include; administration of the HDAC inhibitor three times per day and prednisone once a day. Normally, the steroids are administrated 1-2 times a day depending on the formulation profile and the release profile of the active agent. Administration of the HDAC inhibitor and the steroid may be at least 24-72 hours prior to said immune and/or chemotherapy, such as 30-60, 40-50 or 48 hours prior to immune and/or chemotherapy and the steroid and the HDAC inhibitor may be administered simultaneously or sequentially. However, the administration may be prior to treatment with chemo- and or immunotherapy but it may also be administrated during or after, but prior to is mandatory.

Kit

In one aspect the invention relates to a kit, comprising the pharmaceutical composition in a suitable container or packaging, wherein said composition is described above.

In another aspect the invention relates to a kit comprising a HDAC inhibitor, or a pharmaceutically acceptable acid or a salt thereof or mixture thereof and a steroid or a pharmaceutically acceptable salt thereof or a mixture thereof.

The kit may contain separate containers of the HDAC inhibitor and the steroid. The kit may further comprise an antibody, monoclonal antibody or functional fragments thereof, which binds to CD20. The kit may also contain instructions for use, for example written instructions on how and when to administrate the compounds or composition.

For example, the kit may contain one or more blisters containing a number of tablets or granulates. The active compounds may be mixed in the tablets or granulates or separated into different tablets or granulates as well as separated in the tablets or granulated through barriers such as being coated. The compounds or the pharmaceutical composition may also be kept in the same or separated different pouches in the kit.

The kit may include additional parts, including, for example, appropriate solutions for dilution (e.g., physiological saline solution, glucose solution, etc.), reagents (e.g., for adjusting pH), and devices (e.g., bags, tubes, syringes, needles, transfer sets) for assembly and use (e.g., in the preparation of formulations and subsequent administration).

The written instructions may also include a list of indications for which the formulation (e.g., the HDACi therein) is a suitable treatment as well as how to administer the compound or compounds.

Method of Treatment and Use

The invention also relates to a method of treatment, wherein the above defined composition or compounds are utilized for the treatment of human cancer, such as for the treatment of diseases from the group consisting of sarcoma, malignant melanoma, skin cancer, estrogen receptor-dependent and independent breast cancer, ovarian cancer, prostate cancer, renal cancer, colon and colorectal cancer, pancreatic cancer, head and neck cancer, small cell and non-small cell lung carcinoma, and cancer of blood cells. Examples include the treatment of diseases selected from the group consisting of diffuse large B cell lymphoma (DLBCL), follicular lymphoma, chronic lymphocytic leukaemia, myeloma, Tcell lymphoma and Hodgkin lymphoma.

The term "treatment" is used in the context of treating a condition, pertains generally to treatment and therapy of a human being in which some desired therapeutic effect is achieved.

The term treatment also includes other types of treatment and therapies, in which two or more treatments are combined for example simultaneously or sequentially, such as the steroid and the HDAC inhibitor may be administered simultaneously or sequentially. For example the compounds described herein may be used alone or in combination and for example together with other agents, such as cytotoxic agents etc. Examples include chemotherapy (administration of active agents, such as the disclosed compounds or CHOP). CHOP is a combination of cyclophosphamide, doxorubicin, vincristine and prednisone, which may be administrated in amount of 750+/−10% mg/m$^2$ of cyclophosphamide, 50+/−10% mg/m$^2$ of doxorubicin, 1.4+/−10% mg/m$^2$ of vincristine and 50+/−10% mg/m$^2$ of prednisone Immunotherapy, including antibody, monoclonal antibody or a functional fragment thereof, such as Rituximab, ofatumumab, GA101, tositumumab, ibritumumab, ocraluzumab, veltuzumab, epratuzumab, FTBA05, AME-133V or R603. All the above mentioned antibodies bind to CD20 present on B-cells. The antibodies may be administrated in an amount of 375+/−10% mg/m$^2$. Other examples are prodrugs; surgery, radiation, and gene therapy.

Antibodies are included as therapeutic agents in the methods of the invention, including functional fragments thereof "Antibodies" as used herein includes polyclonal and monoclonal antibodies, chimeric, single chain, and humanized antibodies, as well as Fab fragments, including the products of an Fab or other immunoglobulin expression library. The term antibody as used in this invention is meant to include intact molecules as well as fragments thereof, such as Fab and F(ab').sub.2, Fv and SCA fragments which are capable of binding an epitopic determinant on a protein of interest. A single chain antibody ("SCA") is a genetically engineered single chain molecule containing the variable region of a light chain and the variable region of a heavy chain, linked by a suitable, flexible polypeptide linker.

The present invention concerns human beings. Thus the methods are applicable to human therapy.

Following examples are intended to illustrate, but not to limit, the invention in any manner, shape, or form, either explicitly or implicitly.

EXAMPLES

Biological Evaluation

Inventors of the present invention have established a cell line in vitro model for CD20 antibody-CHOP resistance (CD20 antibody being Rituximab), based on five DLBCL cell lines with differing sensitivity to CD20antibody-CHOP induced cell death (Ageberg, Rydström, Lindén, Linderoth, Jerkeman and Drott; *Exp Cell Research*; May 1; 317(8): 1179-91). In this model, treatment with valproic acid at pharmacological concentrations shows a strong sensitising effect to CHOP mediated cell death. This correlates to an increase in acetylation of histone H3 as measured by western blot analysis. Also, pre-treatment of DLBCL cell lines with a combination of valproic acid and prednisolone for 48 hours further increased their sensitivity to CHOP induced cell death. In addition, also pretreatment with the hydroxamic/carbamic a HDAC inhibitors Trichostatin A and Belinostat sensitized DLBCL cell lines to CHOP-induced cell death, an effect which was potentiated by addition of prednisolone. Moreover, also the steroid dexamethasone potentiated the sensitizing effect to CHOP-induced cell death induced by valproic acid alone. Taken together, the results indicate that a combination of an HDAC inhibitor and a steroid sensitizes Bcell lymphoma cell lines to CHOP-induced cell death. This shows that a combination therapy with an HDAC inhibitor and a steroid will increase the response to chemotherapy or immunochemotherapy in lymphoma treatment.

Example 1

Valproic acid (VPA) sensitises DLBCL Cell Lines to CHOP Treatment.

The DLBCL cell lines WSU-NHL, Karpas-422, ULA, SU-DHL-5 and SU-DHL-8 cells were treated for 72 hours with three different concentrations (0.1 mM, 2 mM and 10 mM respectively) of valproic acid (VPA) alone, or in combination with CHOP. The CHOP regimen used in all examples consists of 10 µM cyclophosphamide monohydrate, 20 nM doxorubicin hydrochloride, 2 nM vincristine sulfate and 20 µg/ml prednisolone. (Ageberg, Rydström, Lindén, Linderoth, Jerkeman and Drott; *Exp Cell Research*; May 1; 317(8):1179-91).

The cell viability was assessed after 72 hours by trypan blue exclusion and normalised to untreated control cells at day 0 (seeding). Data are presented as mean±SEM, n=3.

As shown in Table 1, addition of valproic acid increased the cell death in response to CHOP treatment in all lymphoma cell lines, shows that a combination of valproic acid and CHOP could be beneficial to lymphoma patients.

TABLE 1A

| ULA cells | | | | | | |
|---|---|---|---|---|---|---|
| VPA | −CHOP | | | +CHOP | | |
| concentration | Mean | SEM | N | Mean | SEM | N |
| Control | 100 | 1 | 3 | 66 | 6 | 3 |
| 0.1 mM | 105 | 1 | 3 | 73 | 3e−001 | 3 |
| 2 mM | 52 | 4 | 3 | 52 | 1 | 3 |
| 10 mM | 50 | 4 | 3 | 42 | 6 | 3 |

TABLE 1B

| Karpas-422 cells | | | | | | |
|---|---|---|---|---|---|---|
| VPA | −CHOP | | | +CHOP | | |
| concentration | Mean | SEM | N | Mean | SEM | N |
| Control | 101 | 1 | 3 | 81 | 3 | 3 |
| 0.1 mM | 100 | 2 | 3 | 80 | 1 | 3 |
| 2 mM | 102 | 1 | 3 | 67 | 8 | 3 |
| 10 mM | 21 | 4 | 3 | 21 | 19 | 3 |

TABLE 1C

| WSU-NHL cells | | | | | | |
|---|---|---|---|---|---|---|
| VPA | −CHOP | | | +CHOP | | |
| concentration | Mean | SEM | N | Mean | SEM | N |
| Control | 100 | 2 | 3 | 91 | 4 | 3 |
| 0.1 mM | 99 | 1 | 3 | 63 | 9 | 3 |
| 2 mM | 29 | 4 | 3 | 6 | 3 | 3 |
| 10 mM | 1 | 1 | 3 | 0 | 0 | 3 |

TABLE 1D

| SU-DHL-8 cells | | | | | | |
|---|---|---|---|---|---|---|
| VPA | −CHOP | | | +CHOP | | |
| concentration | Mean | SEM | N | Mean | SEM | N |
| Control | 102 | 2 | 3 | 64 | 1 | 3 |
| 0.1 mM | 105 | 2 | 3 | 55 | 5 | 3 |
| 2 mM | 67 | 11 | 3 | 0 | 0 | 3 |
| 10 mM | 0 | 0 | 3 | 0 | 0 | 3 |

TABLE 1E

| SU-DHL-5 cells | | | | | | |
|---|---|---|---|---|---|---|
| VPA | −CHOP | | | +CHOP | | |
| concentration | Mean | SEM | N | Mean | SEM | N |
| Control | 105 | 5 | 3 | 32 | 1 | 3 |
| 0.1 mM | 124 | 11 | 3 | 26 | 5 | 3 |
| 2 mM | 53 | 2 | 3 | 1 | 1 | 3 |
| 10 mM | 0 | 0 | 3 | 0 | 0 | 3 |

Example 2

Physiologically Relevant Concentrations of Valproic Acid (VPA) Sensitises DLBCL Cell Lines to CHOP Treatment.

The DLBCL cell lines SU-DHL-8 (Table 2A) and WSU-NHL (Table 2B) were treated for 72 hours with 0.5 mM or 1.5 mM VPA alone, or in combination with CHOP. The concentration of 0.5 mM VPA was chosen because it is a normal serum concentration during continuous VPA treatment in patients with epilepsy. The concentration of 1.5 mM VPA was chosen because it is the maximal tolerated serum concentration during 5 day VPA treatment for compassionate use as noted by the inventor.

The cell viability was assessed after 0 (Day 1), 24 (Day 2), 48 (Day 3) and 72 (Day 4) hours respectively, by trypan blue exclusion and normalised to untreated control cells. Data are presented as mean, n=3.

Treatment effects on viability were tested against the effects of CHOP treatment alone. Significant differences were evaluated using Student's unpaired t-test. All tests were two-sided. Effects were considered statistically significant at P<0.05 (*) and P<0.01 (**).

Viability (% of control cells day 1) are shown in Table 2A (SU-DHL-8) and Table 2B (WSU-NHL, n=3) respectively.

As shown in table 2, physiologically relevant concentrations of VPA increased the cell death in response to CHOP treatment in lymphoma cell lines, showing that a combination of physiologically relevant doses of valproic acid and CHOP could be beneficial to lymphoma patients.

TABLE 2A

| SU-DHL-8 | Day 1 | Day 2 | Day 3 | Day 4 |
|---|---|---|---|---|
| Control | 100 | 101 | 103 | 97 |
| CHOP | 100 | 96 | 87 | 69 |
| 0.5 mM VPA | 100 | 102 | 101 | 94 |
| 1.5 mM VPA | 100 | 97 | 64 | 59 |
| 0.5 mM VPA + CHOP | 100 | 89 | 82 | 49 |
| 1.5 mM VPA + CHOP | 100 | 86 | 35 | 16 |

TABLE 2B

| WSU-NHL | Day 1 | Day 2 | Day 3 | Day 4 |
|---|---|---|---|---|
| Control | 100 | 99 | 100 | 101 |
| CHOP | 100 | 98 | 94 | 86 |

TABLE 2B-continued

| WSU-NHL | Day 1 | Day 2 | Day 3 | Day 4 |
|---|---|---|---|---|
| 0.5 mM VPA | 100 | 97 | 99 | 98 |
| 1.5 mM VPA | 100 | 95 | 68 | 36 (**) |
| 0.5 mM VPA + CHOP | 100 | 53 | 84 | 57 (*) |
| 1.5 mM VPA + CHOP | 100 | 87 | 39 | 27 (*) |

Example 3

Valproic Acid (VPA) does not Interfere with Rituximab-Mediated Cellular Cytotoxicity.

To estimate the impact of VPA on the antibody-dependent-cellular cytotoxicity (ADCC) induced by the CD20 antibody Rituximab.

WSU-NHL cells (Table 3A and 3B) or SU-DHL-8 cells (Table 3C and 3D) were labelled with PKH26, either left untreated or incubated with 1.5 mM VPA for 24 hours followed by addition of rituximab at 0, 0.1, or 10 μg/ml NK cells were added as an effector to target cell ratio of 10:1, thereafter the cells were incubated for an additional 20 hours. Dead target cells were identified as double positive for PKH26 and 7-AAD and used as readout of the assay. The data shown demonstrate percentage of dead cells, and representative of two independent experiments. The date show that VPA does not affect Rituximab induced ADCC, compatible with the use of VPA together with CD20 antibodies in lymphoma patients.

TABLE 3A

WSU-NHL cells

| Amount of Rituximab | +NK cells | | | +NK Cells + 1.5 mM VPA | | |
|---|---|---|---|---|---|---|
| (μg/ml) | Mean | SEM | N | Mean | SEM | N |
| 0 | 16 | 1 | 6 | 27 | 4 | 7 |
| 0.1 | 35 | 5 | 6 | 40 | 6 | 7 |
| 1 | 45 | 5 | 6 | 50 | 5 | 7 |
| 10 | 54 | 2 | 6 | 56 | 3 | 7 |

TABLE 3B

WSU-NHL cells

| Amount of Rituximab | +NK cells + CHOP | | | +NK Cells + 1.5 mM VPA + CHOP | | |
|---|---|---|---|---|---|---|
| (μg/ml) | Mean | SEM | N | Mean | SEM | N |
| 0 | 22 | 2 | 5 | 51 | 5 | 5 |
| 0.1 | 45 | 7 | 5 | 60 | 4 | 5 |
| 1 | 54 | 6 | 5 | 60 | 6 | 5 |
| 10 | 61 | 5 | 5 | 66 | 3 | 5 |

TABLE 3C

SU-DHL-8 cells

| Amount of Rituximab | +NK cells | | | +NK Cells + 1.5 mM VPA | | |
|---|---|---|---|---|---|---|
| (μg/ml) | Mean | SEM | N | Mean | SEM | N |
| 0 | 30 | 7 | 3 | 34 | 6 | 3 |
| 0.1 | 38 | 4 | 3 | 43 | 8 | 3 |
| 1 | 50 | 4 | 3 | 49 | 4 | 3 |
| 10 | 60 | 3 | 3 | 58 | 4 | 3 |

TABLE 3D

SU-DHL-8 cells

| Amount of Rituximab | +NK cells + CHOP | | | +NK Cells + 1.5 mM VPA + CHOP | | |
|---|---|---|---|---|---|---|
| (μg/ml) | Mean | SEM | N | Mean | SEM | N |
| 0 | 23 | 2 | 3 | 45 | 2 | 4 |
| 0.1 | 38 | 6 | 3 | 50 | 4 | 4 |
| 1 | 49 | 7 | 3 | 63 | 2 | 4 |
| 10 | 59 | 2 | 3 | 66 | 2 | 4 |

Example 4

Pretreatment with Valproic acid (VPA) Alone Sensitizes DLBCL Cell Lines to CHOP-Treatment. Pretreatment with a Combination of VPA and Prednisolone Significantly Increases Cell Death as Compared to Pretreatment with VPA Alone Pretreatment with VPA before CHOP could theoretically increase the response to CHOP therapy through induction of DNA damage. However, VPA treatment could result in symptoms such as somnolence in a patient. These symptoms could be counteracted by simultaneous treatment with prednisolone. To study the effect of pretreatment with VPA and prednisolone before CHOP, WSU-NHL cells were treated with different combinations of VPA, prednisolone (P, 20 μg/ml)) and CHOP as illustrated below and in FIG. 1. Viability was assessed by trypan blue exclusion at indicated time points (n=3). Significant differences were evaluated using Student's unpaired t-test. All tests were two-sided. Effects were considered statistically significant at *P<0.05, P<0.01, *P<0.001.

As shown in table 4, pretreatment with VPA alone sensitizes lymphoma cell lines to CHOP-treatment. Moreover, addition of prednisolone further increases significantly CHOP-induced cell death as compared to pretreatment with VPA alone. These data shows that pretreatment with a combination of VPA and prednisolone before CHOP therapy, will be beneficial to a lymphoma patient.

| WSU-NHL | 48 h (mean viability/ SEM) | 72 h (mean viability/ SEM) | 96 h (mean viability/ SEM) | P-value (at 96 h compared to CHOP alone) |
|---|---|---|---|---|
| Control | 99/2 | 101/1 | 99/0 | 0.0213* |
| 0.5 mM VPA | 99/1 | 98/2 | 97/2 | 0.0164* |
| 1.5 mM VPA | 76/1 | 65/6 | 52/7 | 0.0347* |
| Prednisolone (P) | 97/1 | 90/3 | 82/2 | 0.3143 |
| 0.5 mM VPA + P | 92/1 | 78/8 | 65/8 | 0.1053 |
| 1.5 mM VPA + P | 45/10 | 31/7 | 18/7 | 0.0056** |
| CHOP | 99/2 | 95/2 | 86/2 | - |
| 0.5 mM VPA + CHOP | 99/1 | 97/2 | 81/1 | 0.1093 |
| 1.5 mM VPA + CHOP | 76/1 | 55/5 | 40/7 | 0.0172* |
| P + CHOP | 97/1 | 85/3 | 69/6 | 0.0936 |
| 0.5 mM VPA + P + CHOP | 92/1 | 73/3 | 55/8 | 0.0568 |
| 1.5 mM VPA + P + CHOP | 45/10 | 24/4 | 16/6 | 0.0034* |

Example 5

Figure 2:
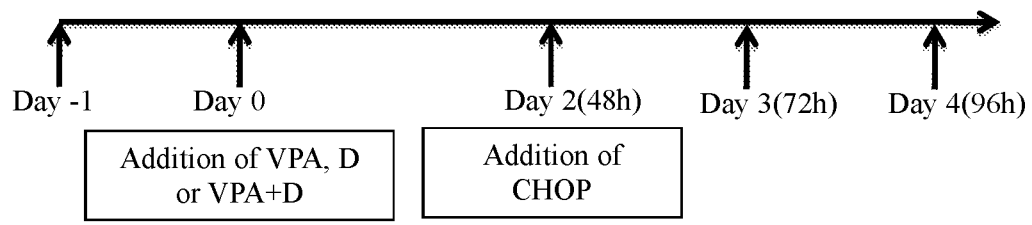
FIG. 2 shows different combinations of VPA, the steroid dexamethasone and CHOP applied to cells in accordance with the present invention.

Pretreatment with a Combination of VPA and the Steroid Dexamethasone Significantly Increases CHOP-Induced Cell Death as Compared to Pretreatment with VPA Alone To study whether other steroids than prednisolone could sensitize to the cell death induced by VPA and CHOP, WSU-NHL cells were treated with different combinations of VPA, the steroid dexamethasone (D, 1 µM) and CHOP as illustrated below and in FIG. 2. Viability was assessed by trypan blue exclusion at indicated time points (n=3). Significant differences were evaluated using Student's unpaired t-test. All tests were two-sided. Effects were considered statistically significant at *P<0.05, P<0.01, *P<0.001.

As shown in table 5, pretreatment with dexamethasone further increases VPA-CHOP-induced cell death as compared to pretreatment with VPA alone. These data shows that pretreatment with a combination of VPA and other steroids, such as dexamethasone before CHOP therapy, will be beneficial to a lymphoma patient.

| WSU-NHL | 48 h (mean viability/ SEM) | 72 h (mean viability/ SEM) | 96 h (mean viability/ SEM) | P-value (at 96 h compared to CHOP alone) |
|---|---|---|---|---|
| Control | 99/2 | 101/1 | 99/0 | 0.0213* |
| 0.5 mM VPA | 99/1 | 98/2 | 97/2 | 0.0164* |
| 1.5 mM VPA | 76/1 | 65/6 | 52/7 | 0.0347* |
| Dexamethasone (D) | 92/1 | 92/3 | 86/4 | 0.9507 |
| 0.5 mM VPA + D | 87/3 | 79/1 | 65/6 | 0.0543 |
| 1.5 mM VPA + D | 50/7 | 25/4 | 18/6 | 0.0039** |
| CHOP | 99/2 | 95/2 | 86/2 | - |
| 0.5 mM VPA + CHOP | 99/1 | 97/2 | 81/1 | 0.1093 |
| 1.5 mM VPA + CHOP | 76/1 | 55/5 | 40/7 | 0.0172* |
| Dexamethasone (D) + CHOP | 92/1 | 85/4 | 64/3 | 0.0047** |
| 0.5 mM VPA + D + CHOP | 87/3 | 78/1 | 58/5 | 0.0127* |
| 1.5 mM VPA + D + CHOP | 50/7 | 30/6 | 21/4 | 0.0003*** |

Example 6

Pretreatment with the HDAC Inhibitor Tricostatin A or Belinostat Sensitizes DLBCL Cell Lines to CHOP-Treatment. Pretreatment with a Combination of Trichostatin A and Prednisolone Significantly Increases CHOP-Induced Cell Death as Compared to Pretreatment with Trichostatin A or Belinostat Alone To study whether pretreatment with HDACinhibitors from other HDACinhibitor subgroups also had a sensitizing effect to CHOP-induced cell death, WSU-NHL cells were treated with different combinations of the hydroxamic/carbamic acid HDACinhibitor Trichostatin A (TSA) and Belinostat, Prednisolone (P, 20 µg/ml) and CHOP as illustrated below. Viability was assessed by trypan blue exclusion at indicated time points (n=3). Significant differences were evaluated using Student's unpaired t-test. All tests were two-sided. Effects were considered statistically significant at *P<0.05, P<0.01, *P<0.001.

As shown in table 6, pretreatment with Trichostatin A alone sensitizes lymphoma cell lines to CHOP-treatment.

Moreover, addition of prednisolone significantly increases CHOP-induced cell death as compared to pretreatment with VPA alone. These data shows that pretreatment with a combination of HDAC inhibitors also from the hydroxamic/carbamic acid group together with prednisolone before CHOP therapy, will be beneficial to a lymphoma patient.

| WSU-NHL | 48 h (mean viability/ SEM) | 72 h (mean viability/ SEM) | 96 h (mean viability/ SEM) | P-value (at 96 h compared to CHOP alone) |
|---|---|---|---|---|
| Control | 100/0 | 100/1 | 100/0 | 0.053455053 |
| 150 nM TSA | 93/2 | 94/1 | 97/1 | 1 |
| 300 nM TSA | 59/3 | 42/2 | 49/1 | 3.56367E−05*** |
| Prednisolone (P) | 99/1 | 98/0 | 98/1 | 0.42039602 |
| 150 nM TSA + P | 89/5 | 87/2 | 87/4 | 0.121321131 |
| 300 nM TSA + P | 60/5 | 36/4 | 32/4 | 0.002160384** |
| CHOP | 100/0 | 101/0 | 97/1 | — |
| 150 nM TSA + CHOP | 93/2 | 86/3 | 87/3 | 0.015277572* |
| 300 nM TSA + CHOP | 59/3 | 45/2 | 37/7 | 0.06838847 |
| P + CHOP | 99/1 | 99/2 | 91/1 | 0.01151857* |
| 150 nM TSA + P + CHOP | 89/5 | 78/1 | 74/2 | 0.00535689** |
| 300 nM TSA + P + CHOP | 60/5 | 36/3 | 24/4 | 0.001812973** |

Belinostat showed similar results (data not shown).

What is claimed is:

1. A method of treating a human being suffering from cancer selected from the group consisting of diffuse large B cell lymphoma (DLBCL), follicular lymphoma, chronic lymphocytic leukaemia, T cell lymphoma and Hodgkin lymphoma, wherein the method comprises the steps of:
   i) pretreating said human by administrating a HDAC inhibitor, a pharmaceutically acceptable acid or a salt thereof or a mixture thereof and a steroid or a pharmaceutically acceptable salt thereof, simultaneously or sequentially, wherein the HDAC inhibitor is selected from the group consisting of valproic acid or valproate semisodium, sodium valproate or magnesium valproate, and wherein the steroid is selected from the group consisting of prednisone, prednisolone, dexamethasone or betamethasone, and
   ii) treating said human by administrating a combination of cyclophosphamide, doxorubicin, vincristine and prednisone (CHOP), or a combination of cyclophosphamide doxorubicin, vincristine, prednisone and CD20 antibody rituximab (R-CHOP),
wherein said step of pretreating said human is performed 24-72 hours prior to said step of treating said human.

2. The method of claim 1, wherein the steroid is prednisone and the prednisone is selected is administered so as to achieve a serum concentration of 20 µg/ml of its metabolite prednisolone in said human.

3. The method of claim 1, wherein the steroid is dexamethasone and the dexamethasone is administered so as to achieve a serum concentration of 1 µM in said human.

4. The method of claim 1, wherein the HDAC inhibitor is valproic acid and wherein the steroid is prednisone.

5. The method of claim 4, wherein the valproic acid is administered so as to achieve a serum concentration of 0.5 mM to 1.5 mM in said human.

6. The method of claim 5, wherein the valproic acid is administered so as to achieve a serum concentration of 0.5 mM or 1.5 mM in said human.

7. The method according to claim 1, wherein said HDAC inhibitor and said steroid are combined in a pharmaceutical composition, said pharmaceutical composition being administered to said human.

8. The method according to claim 2, wherein said step of pretreating said human is performed 48 hours prior to said step of treating said human.

* * * * *